United States Patent
Accisano, III

(10) Patent No.: US 11,806,499 B2
(45) Date of Patent: Nov. 7, 2023

(54) MEDICAL PUSH CONNECTORS

(71) Applicant: Merit Medical Systems, Inc., South Jordan, UT (US)

(72) Inventor: Nicholas Accisano, III, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 783 days.

(21) Appl. No.: 16/773,537

(22) Filed: Jan. 27, 2020

(65) Prior Publication Data
US 2020/0230394 A1 Jul. 23, 2020

Related U.S. Application Data

(62) Division of application No. 15/675,081, filed on Aug. 11, 2017, now Pat. No. 10,543,355.

(60) Provisional application No. 62/377,944, filed on Aug. 22, 2016.

(51) Int. Cl.
*A61M 39/26* (2006.01)
*A61M 39/10* (2006.01)
*A61M 39/24* (2006.01)

(52) U.S. Cl.
CPC .......... *A61M 39/26* (2013.01); *A61M 39/105* (2013.01); *A61M 39/1011* (2013.01); *A61M 2039/1077* (2013.01); *A61M 2039/1083* (2013.01); *A61M 2039/242* (2013.01)

(58) Field of Classification Search
CPC .............. A61M 39/26; A61M 39/1011; A61M 39/105; A61M 2039/1077; A61M 2039/1083; A61M 2039/242; A61M 39/14; F16L 21/08
See application file for complete search history.

(56) References Cited

U.S. PATENT DOCUMENTS

| | | | |
|---|---|---|---|
| 4,440,424 A | 4/1984 | Mode | |
| 4,508,369 A | 4/1985 | Mode | |
| 4,537,183 A * | 8/1985 | Fogarty | A61F 2/26 128/DIG. 25 |
| 4,632,435 A * | 12/1986 | Polyak | B25B 7/02 285/179 |
| 4,895,570 A | 1/1990 | Larkin | |
| 4,917,668 A | 4/1990 | Haindl | |
| 5,215,538 A | 6/1993 | Larkin | |
| 5,570,910 A | 11/1996 | Highlen | |

(Continued)

FOREIGN PATENT DOCUMENTS

| | | |
|---|---|---|
| JP | 20150360046 | 2/2015 |
| WO | 2008136899 | 11/2008 |

OTHER PUBLICATIONS

European Search Report dated Mar. 9, 2020 for EP17844126.7.

(Continued)

*Primary Examiner* — Theodore J Stigell
(74) *Attorney, Agent, or Firm* — Dorsey & Whitney LLP

(57) ABSTRACT

Medical push connectors and systems are provided. A medical push connector can include an engagement member operatively coupled to a release member. The engagement member may releasably couple a medical device to the medical push connector. Medical push connector systems may include one or more medical devices and a medical push connector coupled to, or coupleable to, the one or more medical devices.

15 Claims, 8 Drawing Sheets

(56) References Cited

U.S. PATENT DOCUMENTS

| | | | |
|---|---|---|---|
| 5,762,380 A | * | 6/1998 | Hiwatashi ............... F16L 21/08 285/39 |
| 6,238,211 B1 | | 5/2001 | Esrock |
| 6,250,921 B1 | | 6/2001 | Esrock |
| 7,380,836 B2 | | 6/2008 | Bogdanowicz et al. |
| 9,067,020 B2 | | 6/2015 | Menassa et al. |
| 2002/0039714 A1 | | 4/2002 | Esrock |
| 2006/0061101 A1 | | 3/2006 | Bogdanowicz et al. |
| 2008/0114308 A1 | | 5/2008 | Di Palma et al. |
| 2008/0275403 A1 | | 11/2008 | Maaskamp et al. |
| 2012/0259291 A1 | | 10/2012 | Lareau et al. |
| 2013/0030387 A1 | | 1/2013 | Williams et al. |

OTHER PUBLICATIONS

International Search Report and Written Opinion dated Nov. 10, 2017 for PCT/US2017/046511.
Office Action dated Feb. 1, 2019 for U.S. Appl. No. 15/675,081.
Office Action dated Jun. 17, 2019 for U.S. Appl. No. 15/675,081.

* cited by examiner

MEDICAL PUSH CONNECTORS

RELATED APPLICATIONS

This application is a divisional of U.S. patent application Ser. No. 15/675,081, filed on Aug. 11, 2017 and titled, "Medical Push Connectors," which claims priority to U.S. Provisional Application No. 62/377,944, filed on Aug. 22, 2016 and titled, "Medical Push Connectors" both of which are hereby incorporated by reference in their entireties.

TECHNICAL FIELD

The present disclosure relates generally to medical push connectors. More specifically, the present disclosure relates to medical push connectors configured to couple a first medical device to a second medical device. This disclosure also relates to medical push connector systems including one or more medical devices and a medical push connector coupled to, or coupleable to, the one or more medical devices. Related methods are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1:
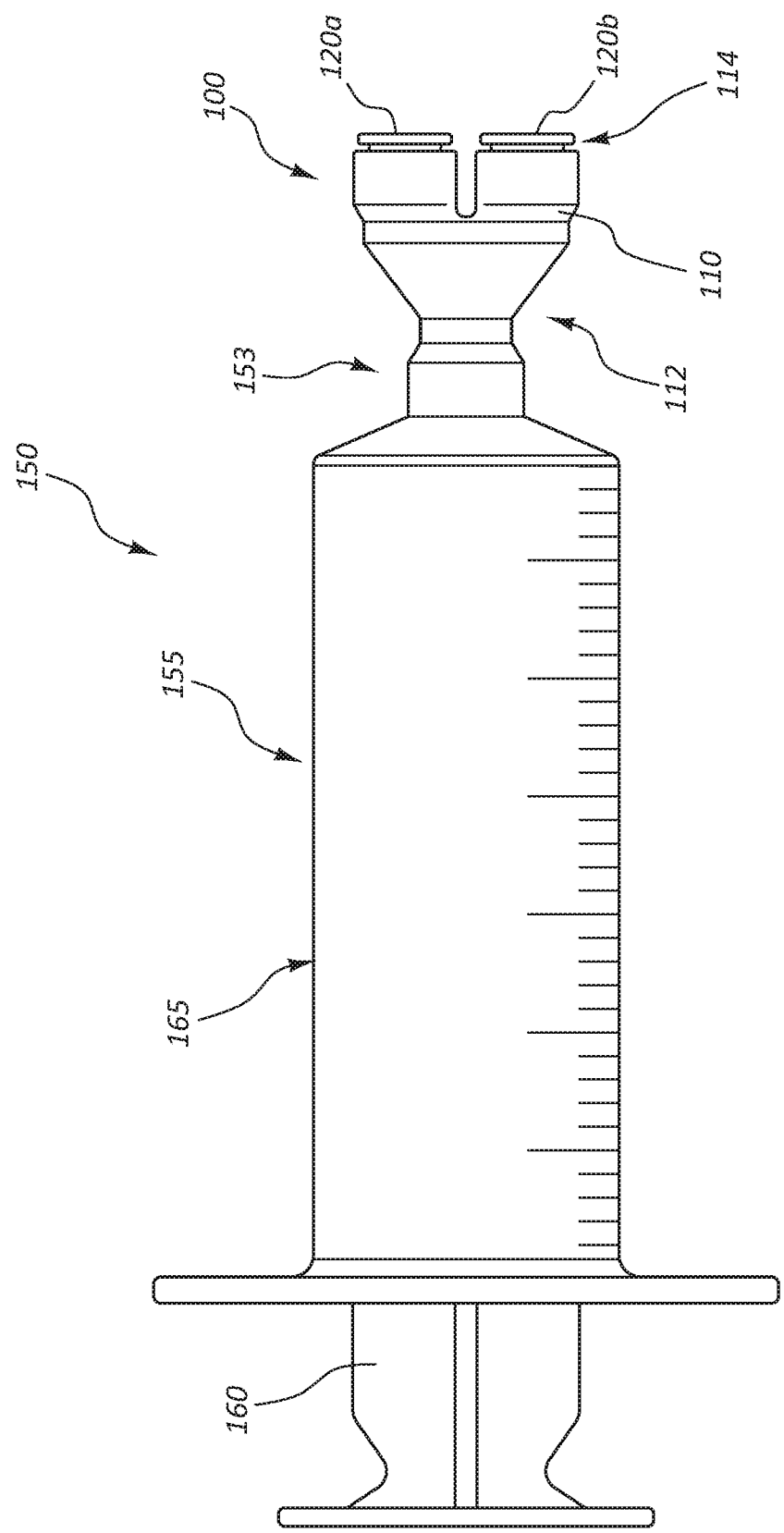
FIG. 1 is a side view of a high-pressure fluid displacement medical device including a medical push connector.

The various embodiments disclosed herein generally relate to medical push connectors and medical push connector systems. In some embodiments, the medical push connector includes an engagement member operatively coupled to a release member. The engagement member may be configured to releasably couple a medical device to the medical push connector. In certain embodiments, the medical push connector systems may include one or more medical devices (e.g., a high-pressure fluid displacement medical device) and a medical push connector coupled to, or configured to be coupled to, the one or more medical devices.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a medical push connector is defined as the end closest to the practitioner during utilization of the medical push connector. The distal end is the end opposite the proximal end, along the longitudinal direction of the medical push connector.

The term "resilient" refers to a component, device, or object having a particular shape that can then be elastically deformed into a different shape, but that may return to the original shape when unconstrained. For example, a resilient element or arm of an engagement member may have a first shape when unconstrained (i.e., when not engaged with a release member) and, in use, the resilient element may then be constrained (i.e., temporarily engaged with the release member) to elastically deform the resilient element into a second shape (i.e., displaced radially outward due to interaction with a portion of the release member), then unconstrained (i.e., removed from engagement with the release member) such that the resilient element returns to its first shape or substantially returns to its first shape.

FIG. 1 is a side view of a high-pressure fluid displacement medical device 150. As depicted, the high-pressure fluid displacement medical device 150 is a syringe. In some embodiments, the high-pressure fluid displacement medical device 150 may be a heart pump, any medical device configured for use at a pressure of greater than about 5 atm (atmospheres), any medical device configured for use at a pressure of greater than about 10 atm, or another suitable medical device. The syringe 150 can include a syringe body 155 and a plunger 160. In some embodiments, the plunger 160 may be configured to be disposed and/or displaceable within at least a portion of a barrel 165 of the syringe body 155.

A medical push connector 100, also referred to herein as a medical connector, may be coupled to or disposed at a distal end 153 of the syringe 150. As illustrated, the medical connector 100 may include a body 110 having a proximal end or first end 112 and a distal end or second end 114. The medical connector 100 may also include a first release member 120*a* and a second release member 120*b*. In some other embodiments, the medical connector 100 may include only one release member. For example, the body 110 may not be Y-shaped (e.g., the body may be I-shaped) and may include only a single release member. In yet some other embodiments, the medical connector 100 may include three, four, or another suitable number of release members.

Figure 2:
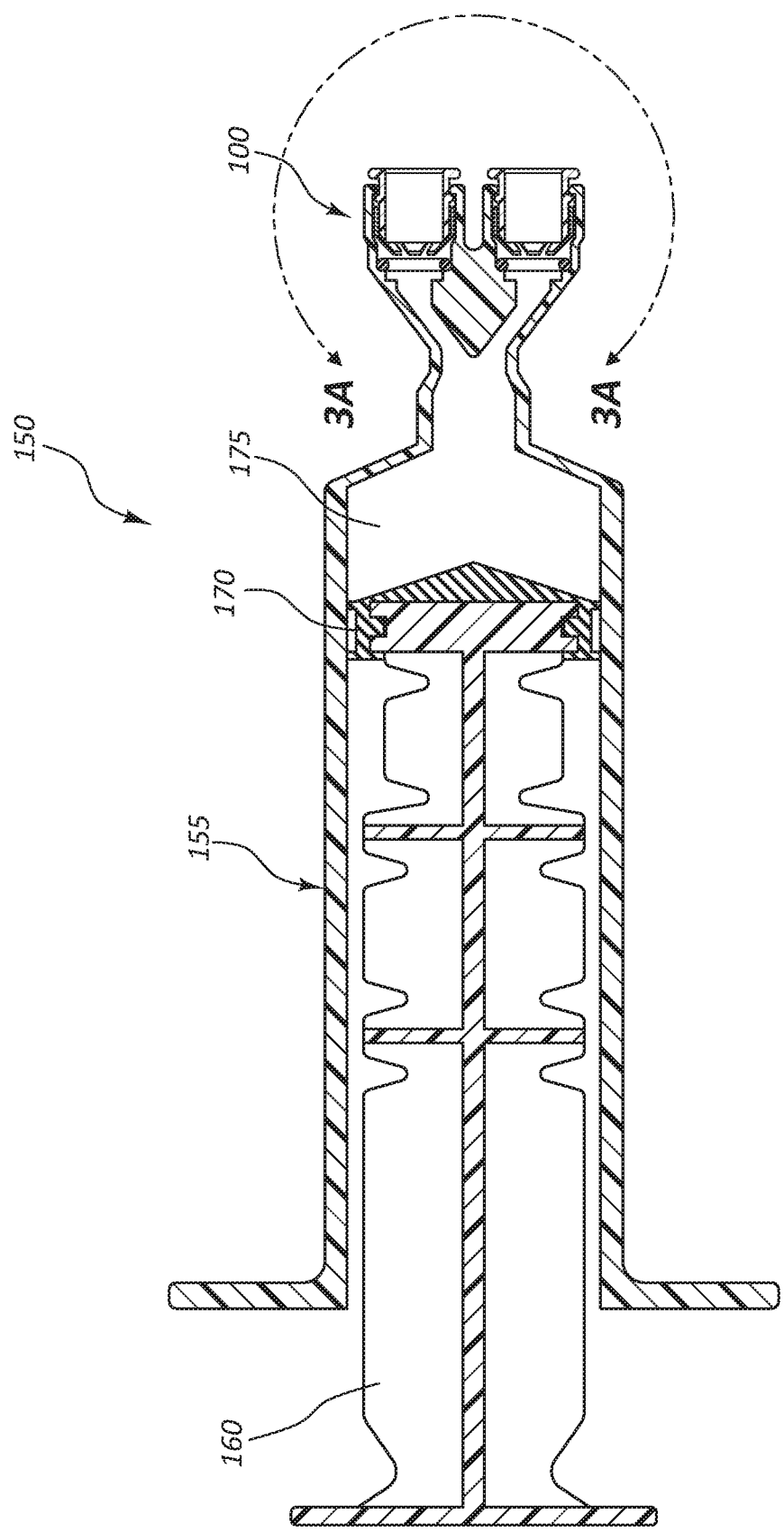
FIG. 2 is a cross-sectional view of the medical device of FIG. 1.

FIG. 2 is a cross-sectional view of the syringe 150 of FIG. 1. As shown, the plunger 160 can include a seal member 170. In certain embodiments, the seal member 170 may be integrally molded with the plunger 160. In certain other embodiments, the seal member 170 may be a discrete component of the syringe 150 and the seal member 170 may be coupled to the plunger 160 (e.g., to a distal end of the plunger 160). A reservoir 175 may be disposed within at least a portion of the syringe body 155. For example, the reservoir 175 may be disposed within the syringe body 155 between each of the seal member 170 and the medical connector 100.

Figure 3A:
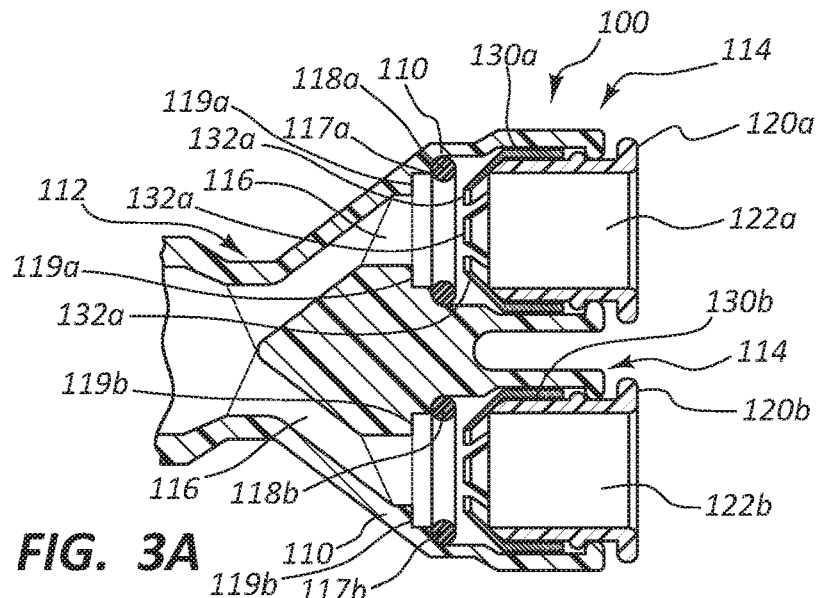
FIG. 3A is a detail view of a portion of the medical device of FIG. 2, indicated by line 3A-3A, in a first configuration.
Figure 3B:
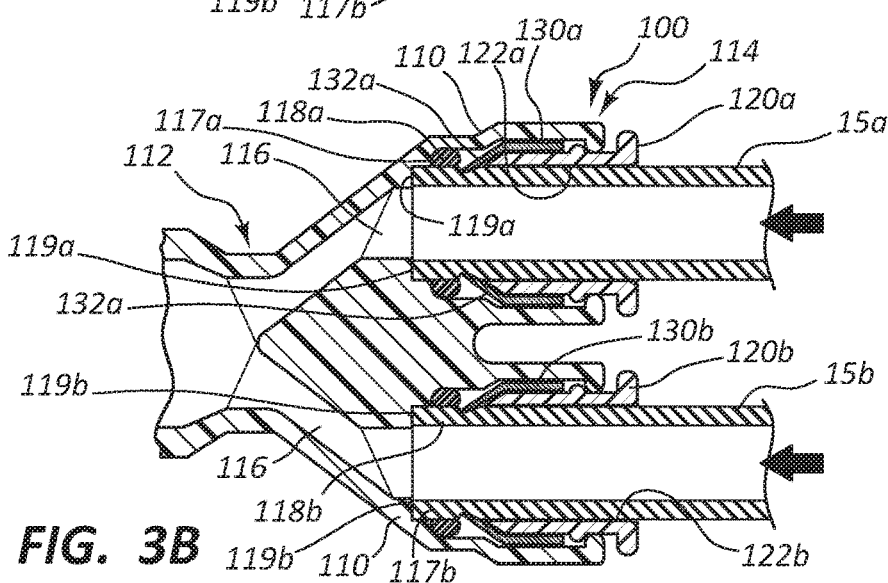
FIG. 3B is a detail view of the portion of the medical device of FIG. 3A in a second configuration.
Figure 3C:
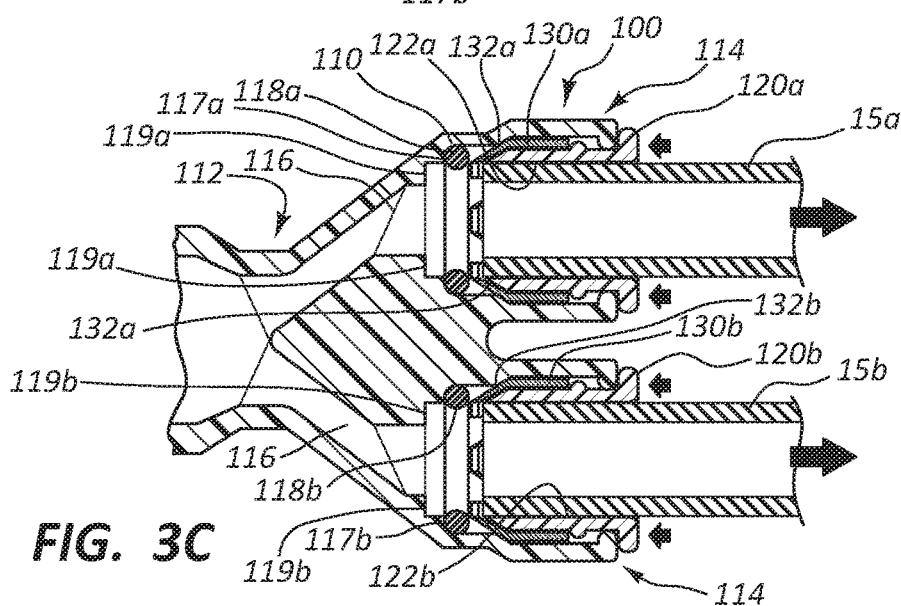
FIG. 3C is a detail view of the portion of the medical device of FIG. 3A in a third configuration.

FIG. 3A is a detail view of the medical connector 100 of the syringe 150 of FIG. 2, indicated by line 3A-3A, in a first configuration. FIG. 3B is a detail view of the medical connector 100 in a second configuration, and FIG. 3C depicts the medical connector 100 in a third configuration. As discussed above, the medical connector 100 can include a body 110 having a proximal end 112 and a distal end 114. A body lumen 116 can extend through at least a portion of the body 110. For example, the body lumen 116 may extend between the proximal end 112 and the distal end 114 of the body 110 such that there is fluid communication between the proximal end 112 and the distal end 114.

A first release member 120*a* can be coupled to the body 110 at or adjacent the distal end 114 of the body 110. As shown, the first release member 120*a* can include a first release member lumen 122*a*, wherein the first release member lumen 122*a* is in communication (e.g., fluid communication) with the body lumen 116. The first release member lumen 122*a* can extend through at least a portion of the first release member 120*a*. For example, the first release member lumen 122*a* can extend between each of a distal end and a proximal end of the first release member 120*a*.

The medical connector 100 can further include a first engagement member 130*a*. In some embodiments, the first engagement member 130*a* may be operatively coupled to the first release member 120*a*. In certain embodiments, the first engagement member 130*a* may be configured to releasably couple a medical device to the medical connector 100. For example, a practitioner may dispose at least a portion of a first elongate medical device 15*a* within at least a portion of the first release member lumen 122*a*, and at least a portion of the first engagement member 130*a* may be configured to engage at least a portion of the first elongate medical device 15*a* such that the first elongate medical device 15*a* is coupled to the medical connector 100.

In various embodiments, the first engagement member 130*a* can include one or more resilient elements or arms 132*a*. For example, the first engagement member 130*a* can include one, two, three, four, or more resilient elements 132*a*. The one or more resilient elements 132*a* may be configured to engage a medical device when the medical device is disposed within at least a portion of the body lumen 116 (e.g., via the first release member lumen 122*a*). For example, the one or more resilient elements 132*a* may be configured to engage and/or interact with an outer surface of the first elongate medical device 15*a*. In some embodiments, the resilient elements 132*a* may comprise angled tabs configured to frictionally engage with and/or bite or cut into an outside diameter of the elongate medical device 15*a*. The resilient elements 132*a* may be disposed at an angle relative to the longitudinal axis of the elongate medical device 15*a* to facilitate this engagement.

Further, the resilient elements 132*a* may be configured to deflect radially outward as the elongate medical device 15*a* is inserted into the medical connector 100 to engage with the elongate medical device 15*a* and to prevent the elongate medical device 15*a* from being pulled from the medical connector 100.

In certain embodiments, the medical connector 100 may be configured to couple the first elongate medical device 15*a* in a coupling state. Further, the medical connector 100 may be configured to uncouple the first elongate medical device 15*a* in an uncoupling state. In the coupling state (see FIG. 3B), the first release member 120*a* may be disengaged from, or configured to be disengaged from, the one or more resilient elements 132*a* such that at least a portion of each of the one or more resilient elements 132*a* deflects radially inward relative to a longitudinal axis of the first release member lumen 122*a*. Stated another way, the first release member 120*a* may be disposed such that it does not interact with the one or more resilient elements 132*a* in the coupling state.

In the uncoupling state (see FIG. 3C), the first release member 120*a* may be configured to engage or interact with the one or more resilient elements 132*a* such that at least a portion of each of the one or more resilient element 132*a* deflects radially outward relative to a longitudinal axis of the first release member lumen 122*a*. Stated another way, a practitioner may "push" or actuate the first release member 120*a* such that at least a portion of the first release member 120*a* engages with the one or more resilient elements 132*a* to disengage the one or more resilient elements 132*a* from the first elongate medical device 15*a*. Accordingly, upon "pushing" or actuation of the first release member 120*a* by the practitioner, the first elongate medical device 15*a* may be uncoupled from the medical connector 100. That is, "pushing" or actuation of the first release member 120*a* can transition the medical push connector 100 from the coupling state to the uncoupling state.

The medical connector 100 can further include a first seal 118*a* (e.g., an O-ring seal). The first seal 118*a* can be disposed within at least a portion of the body lumen 116. As illustrated, the first seal 118*a* is disposed within the body lumen 116 at a position at or adjacent the proximal end of the first release member lumen 122*a*. Further, the first seal 118*a* can be disposed on or adjacent a first shoulder 117*a*. In various embodiments, the first seal 118*a* may be configured to sealingly engage a medical device (e.g., the first elongate medical device 15*a*) when at least a portion of the first medical device is disposed within the body lumen 116. For example, as shown in FIG. 3B the first seal 118a may seal against an outside diameter of the elongate medical device 15a.

With reference to FIG. 3B, a practitioner may dispose at least a portion of the first elongate medical device 15a (as indicated by the arrow) through the first release member lumen 122a of the first release member 120a and into at least a portion of the body lumen 116. Upon such a disposition of the first elongate medical device 15a, the first seal 118a may engage and/or interact with at least a portion of the first elongate medical device 15a (e.g., an outside diameter of the first elongate medical device 15a) and form a seal between the first seal 118a, the medical connector 100, and/or the first elongate medical device 15a.

In various other embodiments, the medical connector 100 may lack a first seal 118a. Accordingly, the first shoulder 117a may be configured to sealingly engage the first elongate medical device 15a when at least a portion of the first elongate medical device 15a is disposed within the body lumen 116.

As depicted in FIGS. 3A-3C, a second release member 120b can also be coupled to the body 110 at or adjacent the distal end 114 of the body 110. As depicted, the second release member 120b can be coupled to the body 110 at or adjacent the distal end 114 of the body 110 at a position adjacent to and/or displaced from the position wherein the first release member 120a is coupled to the body 110. Analogous to the first release member 120a, the second release member 120b can include a second release member lumen 122b in communication with the body lumen 116. The second release member lumen 122b can extend through at least a portion of the second release member 120b.

The medical connector 100 can further include a second engagement member 130b. In some embodiments, the second engagement member 130b may be operatively coupled to the second release member 120b. In certain embodiments, the second engagement member 130b may be configured to releasably couple a medical device (e.g., a second elongate medical device 15b) to the medical connector 100.

The medical connector 100 can further include a second seal 118b (e.g., an O-ring seal). The second seal 118b can be disposed within at least a portion of the body lumen 116. As illustrated, the second seal 118b is disposed within the body lumen 116 at a position adjacent the proximal end of the second release member lumen 122b. Further, the first seal 118a can be disposed on or adjacent a second shoulder 117b. With reference to FIG. 3B, a practitioner may dispose at least a portion of a second elongate medical device 15b (as indicated by the arrow) through the second release member lumen 122b of the second release member 120b and into at least a portion of the body lumen 116. Upon such a disposition of the second elongate medical device 15b, the second seal 118b may engage and/or interact with at least a portion of the second elongate medical device 15b and form a seal between the second seal 118b, the medical connector 100, and/or the second elongate medical device 15b.

In various other embodiments, the medical connector 100 may lack a second seal 118b. Accordingly, the second shoulder 117b may be configured to sealingly engage the second elongate medical device 15b when at least a portion of the second elongate medical device 15b is disposed within the body lumen 116.

The medical connector 100 may further include a first proximal shoulder 119a disposed proximal of the first shoulder 117a and a second proximal shoulder 119b disposed proximal of the second shoulder 117b. The first and second proximal shoulders 119a, 119b may interact with a proximal end of the elongate medical devices 15a, 15b to provide a positive proximal stop for the elongate medical devices 15a, 15b with respect to the medical connector 100. For example, in the configuration shown in FIG. 3B the proximal ends of the elongate medical devices 15a, 15b are disposed in contact with the first and second proximal shoulders 119a, 119b.

As illustrated, the body lumen 116 of the medical connector 100 is substantially Y-shaped. Stated another way, the body lumen 116 includes three openings, wherein two openings are disposed at or adjacent the distal end 114 of the body 110, and a third opening is disposed at or adjacent the proximal end 112 of the body 110 (e.g., the third opening, as depicted, can be disposed between the body lumen 116 and the reservoir 175 of the syringe 150 (see FIG. 2)). Other configurations of the medical connector 100 are also within the scope of this disclosure. For example, in some embodiments, the medical connector may only include one release member, seal, and/or engagement member. In some other embodiments, the medical connector may include three or more release members, seals, and/or engagement members. Other embodiments of medical connectors are also described in further detail below.

Figure 4:
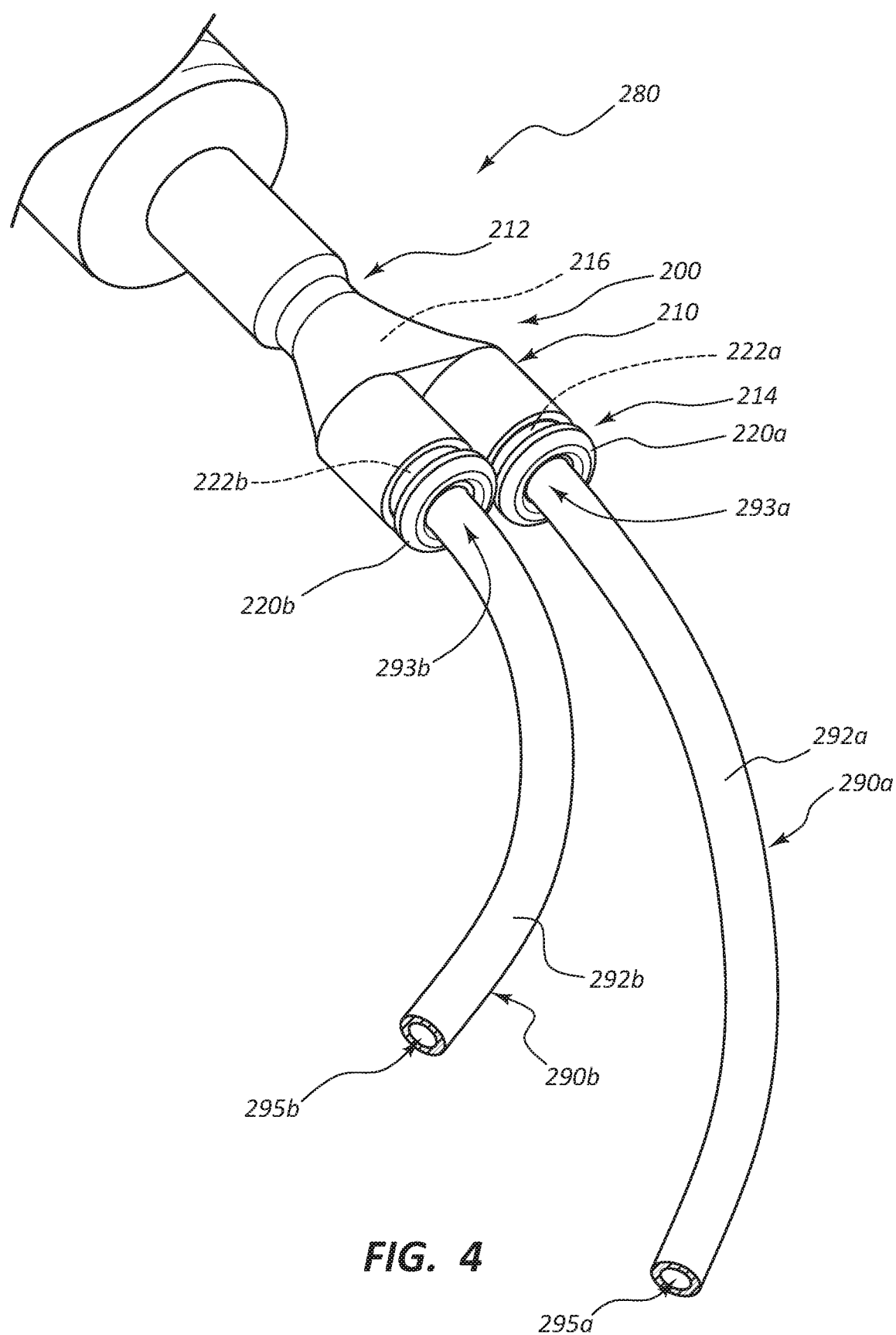
FIG. 4 is a perspective view of a portion of a medical push connector system.
Figure 5:
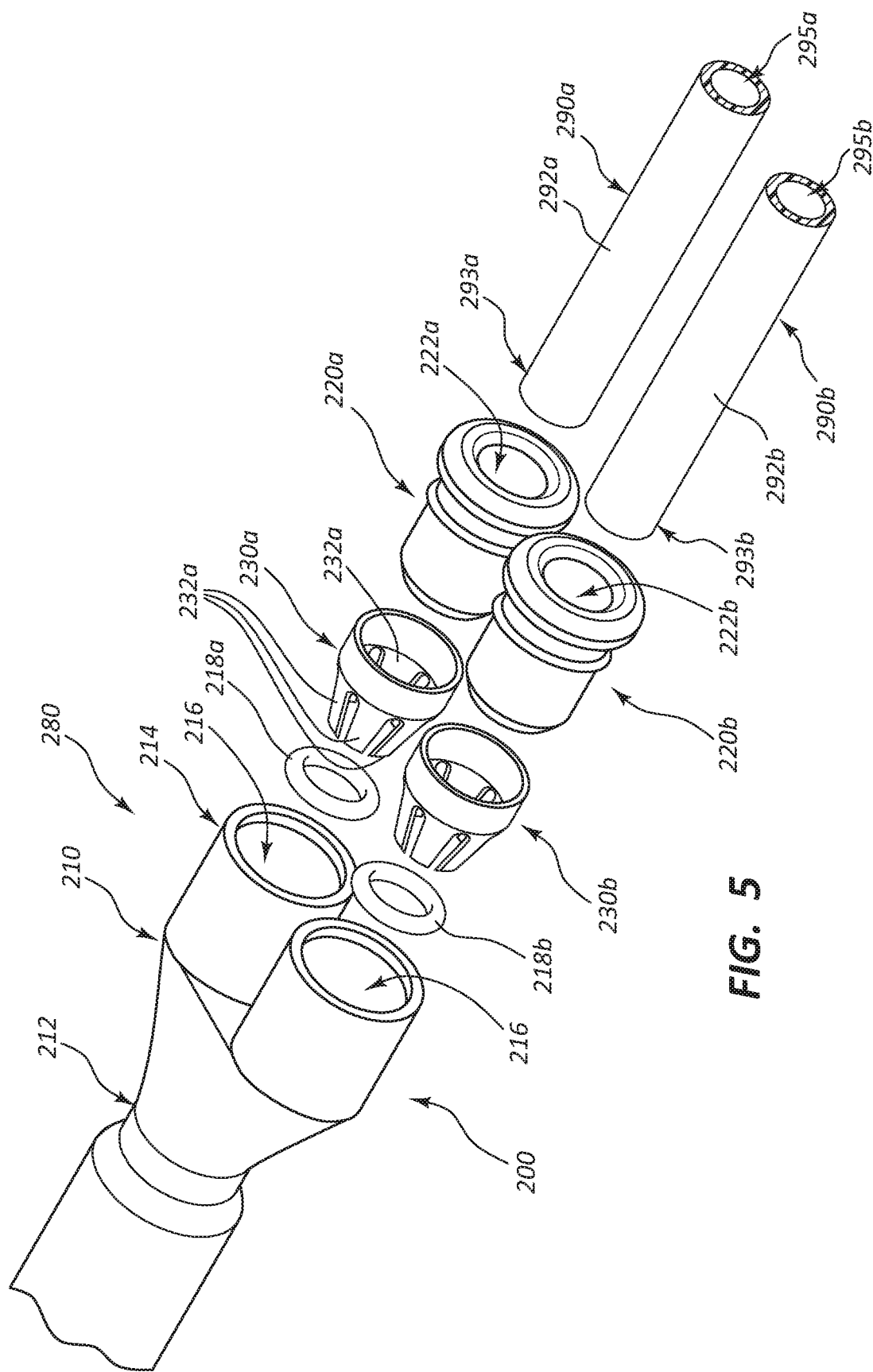
FIG. 5 is an exploded view of a portion of the medical push connector system of FIG. 4.

FIGS. 4 and 5 illustrate a medical push connector system 280, also referred to herein as a medical connector system, including an embodiment of a medical connector 200 that can, in certain respects, resemble components of the medical connector 100 described in connection with FIGS. 1-3C. It will be appreciated that all the illustrated embodiments may have analogous features. Accordingly, like features are designated with like reference numerals, with the leading digits incremented to "2." For instance, the body is designated as "110" in FIGS. 1-3C, and an analogous body is designated as "210" in FIGS. 4 and 5. Relevant disclosure set forth above regarding similarly identified features thus may not be repeated hereafter. Moreover, specific features of the medical connector 100 and related components shown in FIGS. 1-3C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical connector 200 of FIGS. 4 and 5. Any suitable combination of the features, and variations of the same, described with respect to the medical connector 100 and components illustrated in FIGS. 1-3C can be employed with the medical connector 200 and components of FIGS. 4 and 5, and vice versa. This pattern of disclosure applies equally to further embodiments depicted in subsequent figures and described hereafter.

FIG. 4 illustrates a portion of a medical connector system 280. FIG. 5 is an exploded view of the portion of the medical connector system 280 of FIG. 4. In some embodiments, the medical connector system 280 may include a medical connector 200. The medical connector 200 may include a body 210, wherein the body 210 has a proximal end or first end 212 and a distal end or second end 214. A body lumen 216 may also extend through at least a portion of the body 210. For example, the body lumen 216 may extend between the proximal end 212 and the distal end 214 of the body 210 and/or the medical connector 200.

In certain embodiments, a first release member 220a may be coupled to the body 210 at or adjacent the distal end 214 of the body 210. As depicted, the medical connector 200 may include two release members 220a, 220b. In some embodiments, the medical connector 200 may include only one release member. In some other embodiments, the medical connector 200 may include three, four, five, or more release members. In yet some other embodiments, as discussed in further detail below, the medical connector 200 may lack a release member. With reference to FIGS. 4 and 5, the first release member 220a may include a first release member lumen 222a in communication (e.g., fluid communication) with the body lumen 216. Analogously, the second release member 220b may include a second release member lumen 222b that is also in communication with the body lumen 216.

The first release member 220a may be operatively coupled to, or may be configured to be operatively coupled to, a first engagement member 230a. Analogously, the second release member 220b may be operatively coupled to, or may be configured to be operatively coupled to, a second engagement member 230b.

The medical connector system 280 may also include one or more elongate medical devices 290a, 290b. FIGS. 4 and 5 depict only a portion of each of the elongate medical devices 290a, 290b. The first elongate medical device 290a may include an elongate member 292a, wherein the elongate member 292a has a proximal or first end 293a and a distal or second end (not shown). Analogously, the second elongate medical device 290b may include an elongate member 292b, wherein the elongate member 292b has a proximal or first end 293b and a distal or second end (not shown). Furthermore, a first or second elongate member lumen 295a, 295b may be disposed within a portion of each of the first or second elongate member 292a, 292b, respectively. The first and second elongate member lumens 295a, 295b may extend from the first ends 293a, 293b, respectively, along at least a portion of the lengths of the first and second elongate members 292a, 292b, respectively. In various embodiments, the first engagement member 230a may releasably couple, or may be configured to releasably couple, at least a portion of the medical connector 200 to the first end 293a of the first elongate medical device 290a. Analogously, the second engagement member 230b may releasably couple, or may be configured to releasably couple, at least a portion of the medical connector 200 to the first end 293b of the second elongate medical device 290b.

In some embodiments, an elongate medical device may be a thin-walled elongate medical device. An elongate medical device including a thin wall may permit greater fluid flow through a lumen of the thin-walled elongate medical device than another elongate medical device having a thicker wall and a substantially similar outside diameter. The thin-walled elongate medical device may further have a hardened and/or reinforced end such that the thin-walled elongate medical device may be coupled to a medical connector without damaging or compromising the integrity of the thin-walled elongate medical device.

The first engagement member 230a may include one or more resilient elements or arms 232a. In some embodiments, the first engagement member 230a may include one, two, three, four, five, or more resilient elements 232a. Furthermore, at least a portion of the first release member 220a may be configured to engage at least a portion of the one or more resilient elements 232a such that at least a portion of the one or more resilient elements 232a is displaced radially outward relative to a longitudinal axis of the first release member lumen 222a in an uncoupling state (e.g., a state wherein an elongate medical device is uncoupled or disengaged from the medical connector). The first release member 220a is further configured to be disengaged from the one or more resilient elements 232a such that at least a portion of the one or more resilient elements 232a is displaced radially inward relative to the longitudinal axis of the first release member lumen 222a in a coupling state (e.g., a state wherein an elongate medical device is coupled or engaged to the medical connector). The second engagement member 230b may be configured in a manner analogous to the first engagement member 230a, as discussed above.

With reference to FIG. 5, a first seal 218a may be disposed within at least a portion of the body lumen 216. In some embodiments, the first seal 218a may be configured to sealably engage the first end 293a of the first elongate medical device 290a when the first elongate medical device 290a is disposed within at least a portion of the body lumen 216. For example, at least a portion of the first end 293a of the first elongate medical device 290a may press against or engage at least a portion of the first seal 218a to form a seal. Furthermore, a second seal 218b may be configured to be disposed within at least another portion of the body lumen 216. In some embodiments, the second seal 218b may be configured to sealably engage the first end 293b of the second elongate medical device 290b when the second elongate medical device 290b is disposed within at least a portion of the body lumen 216. For example, at least a portion of the first end 293b of the second elongate medical device 290b may press against or engage at least a portion of the second seal 218b to form a seal.

In various embodiments, the medical connector 200 may lack the first seal 218a and/or the second seal 218b. Accordingly, a first shoulder and/or a second shoulder (analogous the first and second shoulders 117a, 117b as discussed above in reference to FIGS. 3A-3C) may be configured to sealingly engage the first and/or second elongate medical devices 290a, 290b when at least a portion of the first and/or second elongate medical devices 290a, 290b are disposed within the body lumen 216.

Figure 6A:
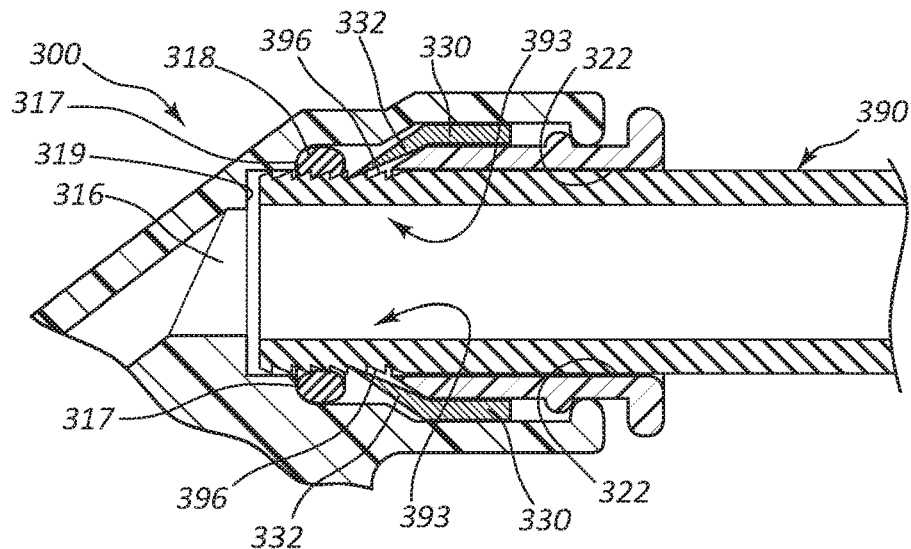
FIG. 6A is a detail view of a portion of the medical push connector system of FIGS. 4 and 5 coupled to an elongate medical device.

FIG. 6A is a cross-sectional detail view of an elongate medical device 390 coupled to a portion of a medical connector 300 (e.g., as part of a medical connector system). As depicted, the elongate medical device 390 may include a high friction zone 396. In some embodiments, the high friction zone 396 may be disposed on at least a portion of an outside surface of the elongate medical device 390. For example, the high friction zone 396 may be an annular high friction zone 396 that is disposed around the outer surface of the elongate medical device 390 at or adjacent a proximal or first end 393 of the elongate medical device 390. The high friction zone 396 may engage, or be configured to engage, at least a portion of an engagement member 330, for example, when at least a portion of the elongate medical device 390 is disposed within at least a portion of a release member lumen 322. In the coupling state, as discussed above, one or more resilient elements or arms 332 of the engagement member 330 may be configured to engage the high friction zone 396 when at least a portion of the elongate medical device 390 is disposed within the release member lumen 322 and/or a body lumen 316. The high friction zone 396 may be configured to enhance the coupling of the medical connector 300 to the elongate medical device 390 in comparison to an elongate medical device lacking a high friction zone. For example, one or more radially projecting surfaces of the high friction zone 396 can engage with the one or more resilient elements 332 of the engagement member 330 to securely couple the elongate medical device 390 to the medical connector 300.

As discussed above, a seal 318 may also be disposed within at least a portion of the body lumen 316 (e.g., on or adjacent a shoulder 317), wherein the seal 318 is configured to engage at least a portion of the elongate medical device 390 (e.g., to form a seal between the medical connector 300 and the elongate medical device 390 in the coupling state). As depicted, the seal 318 may be compressed upon engagement with the elongate medical device 390 such that a seal is formed between the seal 318 and the elongate medical device 390.

In certain embodiments, the medical connector 300 may lack the seal 318. Accordingly, the shoulder 317 may be configured to sealingly engage the elongate medical device 390 when at least a portion of the elongate medical device 390 is disposed within the body lumen 316. The medical connector 300 may further comprise a proximal shoulder 319 which may provide a positive stop for the elongate medical device 390 with respect to the medical connector 300. As shown, the elongate medical device 390 need not be in contact with the proximal shoulder 319 in order for the elongate medical device 390 to be coupled to, and sealed with, the medical connector 300.

Figure 6B:
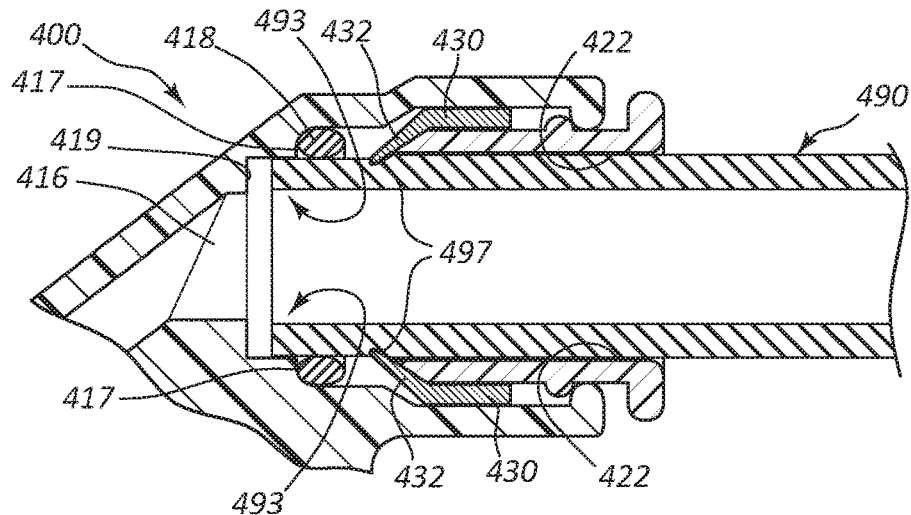
FIG. 6B is a detail view of the portion of the medical push connector system of FIG. 6A coupled to another embodiment of an elongate medical device.

FIG. 6B is a cross-sectional view of another embodiment of an elongate medical device 490 coupled to a portion of a medical connector 400 (e.g., as part of a medical connector system). As depicted, the elongate medical device 490 may include a channel or depression 497 disposed along or on at least a portion of an outside surface of the elongate medical device 490. For example, the depression 497 may be an annular depression that is disposed around the outer surface of the elongate medical device 490 at or adjacent a proximal or first end 493 of the elongate medical device 490. The depression 497 may engage, or be configured to engage, at least a portion of an engagement member 430, for example, when at least a portion of the elongate medical device 490 is disposed within at least a portion of a release member lumen 422. In the coupling state, as discussed above, one or more resilient elements or arms 432 of the engagement member 430 may be configured to engage the depression 497 when at least a portion of the elongate medical device 490 is disposed within the release member lumen 422 and/or the body lumen 416. Analogous to the high friction zone 396, the depression 497 may be configured to enhance the coupling of the medical connector 400 to the elongate medical device 490 in comparison to an elongate medical device lacking a depression. For example, the depression 497 can engage with the one or more resilient elements 432 of the engagement member 430 to securely couple the elongate medical device 490 to the medical connector 400.

As discussed above, a seal 418 may also be disposed within at least a portion of the body lumen 416 (e.g., on or adjacent a shoulder 417), wherein the seal 418 is configured to engage the elongate medical device 490 (e.g., to form a seal between the medical connector 400 and the elongate medical device 490 in the coupling state).

In certain embodiments, the medical connector 400 may lack the seal 418. Accordingly, the shoulder 417 may be configured to sealingly engage the elongate medical device 490 when at least a portion of the elongate medical device 490 is disposed within the body lumen 416. The medical connector 400 may further comprise a proximal shoulder 419 which may provide a positive stop for the elongate medical device 490 with respect to the medical connector 400. As shown, the elongate medical device 490 need not be in contact with the proximal shoulder 419 in order for the elongate medical device 490 to be coupled to, and sealed with, the medical connector 400.

Figure 6C:
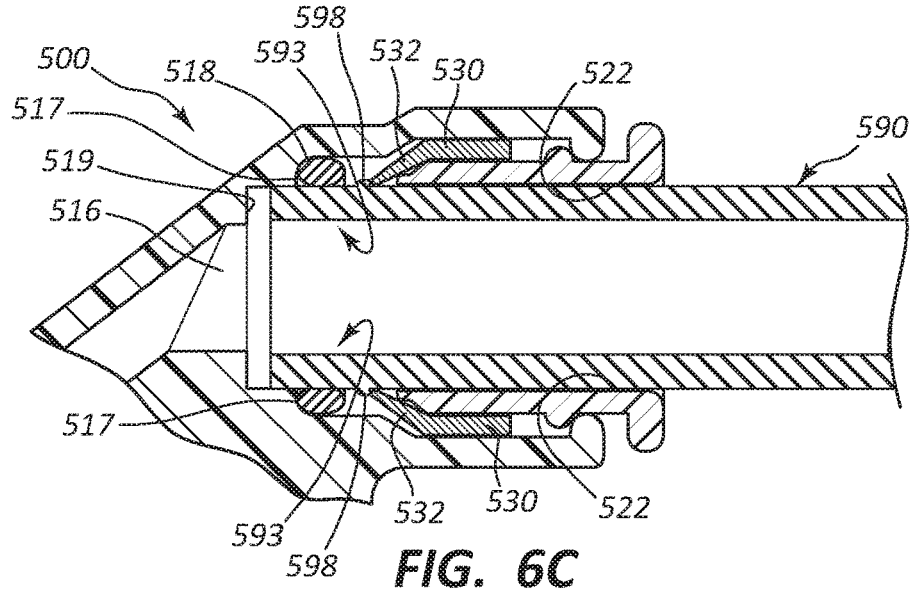
FIG. 6C is a detail view of the portion of the medical push connector system of FIG. 6A coupled to yet another embodiment of an elongate medical device.

FIG. 6C is a cross-sectional view of yet another embodiment of an elongate medical device 590 coupled to a portion of a medical connector 500 (e.g., as part of a medical connector system). As depicted, the elongate medical device 590 may include a ridge 598 disposed on at least a portion of an outside surface of the elongate medical device 590. For example, the ridge 598 may be an annular ridge that is disposed around the outer surface of the elongate medical device 590 at or adjacent a proximal or first end 593 of the elongate medical device 590. The ridge 598 may engage, or be configured to engage, at least a portion of an engagement member 530, for example, when at least a portion of the elongate medical device 590 is disposed within at least a portion of a release member lumen 522. In the coupling state, as discussed above, one or more resilient elements or arms 532 of the engagement member 530 may be configured to engage the ridge 598 when at least a portion of the elongate medical device 590 is disposed within the release member lumen 522 and/or a body lumen 516. Analogous to the high friction zone 396 and/or the depression 497, the ridge 598 may be configured to enhance the coupling of the medical connector 500 to the elongate medical device 590 in comparison to an elongate medical device lacking a ridge. For example, the ridge 598 can engage with the one or more resilient elements 532 of the engagement member 530 to securely couple the elongate medical device 590 to the medical connector 500.

As discussed above, a seal 518 may also be disposed within at least a portion of the body lumen 516 (e.g., on or adjacent a shoulder 517), wherein the seal 518 is configured to engage the elongate medical device 590 (e.g., to form a seal between the medical connector 500 and the elongate medical device 590 in the coupling state).

In certain embodiments, the medical connector 500 may lack the seal 518. Accordingly, the shoulder 517 may be configured to sealingly engage the elongate medical device 590 when at least a portion of the elongate medical device 590 is disposed within the body lumen 516. The medical connector 500 may further comprise a proximal shoulder 519 which may provide a positive stop for the elongate medical device 590 with respect to the medical connector 5300. As shown, the elongate medical device 590 need not be in contact with the proximal shoulder 519 in order for the elongate medical device 590 to be coupled to, and sealed with, the medical connector 500.

Figure 7:
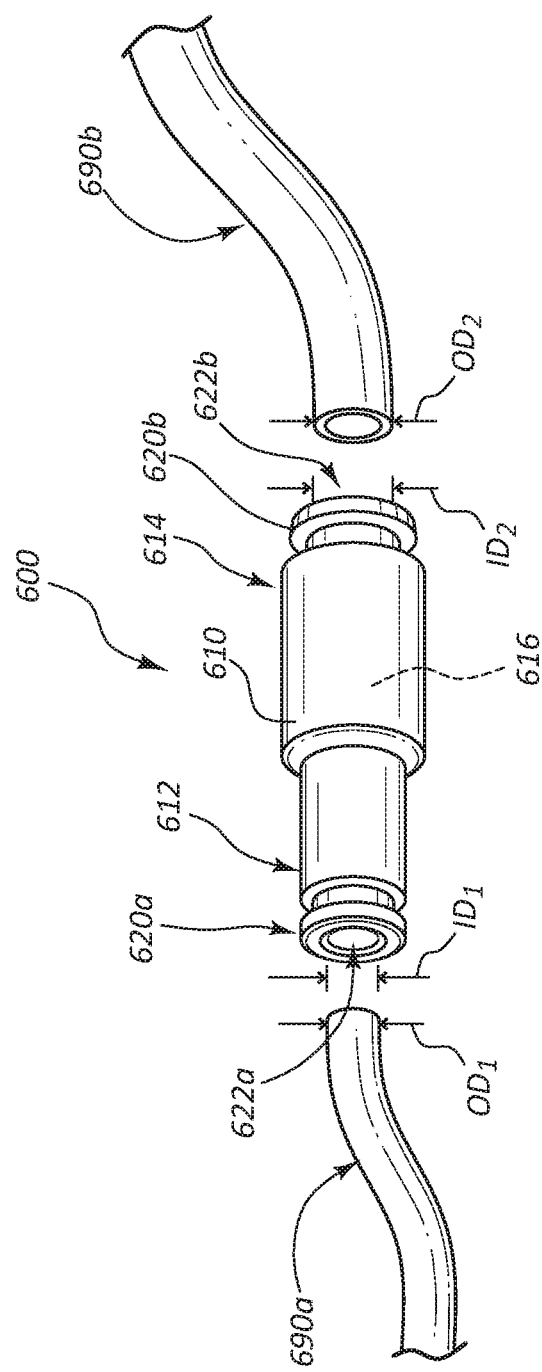
FIG. 7 is a perspective view of another embodiment of a medical push connector.

FIG. 7 is a perspective view of a medical connector 600. As depicted, the medical connector 600 may include a first release member 620a coupled to a body 610, wherein the first release member 620a is coupled to the body 610 at or adjacent a first end 612 of the body 610. The medical connector 600 may further include a second release member 620b coupled to the body 610, wherein the second release member 620b is coupled to the body 610 at or adjacent a second end 614 of the body 610. The first release member 620a may include a first release member lumen 622a in communication with a body lumen 616 of the medical connector 600. Analogously, the second release member 620b may include a second release member lumen 622b in communication with the body lumen 616. Stated another way, each of the first release member lumen 622a and the second release member lumen 622b may be in communication with each other (e.g., fluid communication) via the body lumen 616.

Analogous to the release members discussed above, each of the first and second release members 620a, 620b may be operatively coupled to an engagement member. The first release member 620a may be configured to releasably couple a first elongate medical device 690a to the medical connector 600. Further, the second release member 620b may be configured to releasably couple a second elongate medical device 690b to the medical connector 600.

As illustrated, the medical connector 600 may be configured to couple the first elongate medical device 690a having a first outside diameter $OD_1$ to the second elongate medical device 690b having a second outside diameter $OD_2$. In some embodiments, the first outside diameter $OD_1$ may be less than the second outside diameter $OD_2$, or vice versa. For example, the first elongate medical device 690a may be a 6 French catheter and the second elongate medical device 690b may be a 10 French catheter. Accordingly, the medical connector 600 may couple a 6 French catheter to a 10 French catheter, or vice versa. Other suitable sizes of elongate medical devices are also within the scope of this disclosure. For example, the size of the first elongate medical device may be 4 French, 6 French, 8 French, 10 French, or any other suitable size. Likewise, the size of the second elongate medical device may be 8 French, 10 French, 12 French, 15 French, or any other suitable size.

Stated another way, the first release member 620a may have a first inside diameter $ID_1$ while the second release member 620b may have a second inside diameter $ID_2$. In various embodiments, the first inside diameter $ID_1$ may be less than the second inside diameter $ID_2$, or vice versa. For example, the first release member 620a may be configured to receive and/or releasably couple the first elongate medical device 690a, wherein the first elongate medical device 690a may be an 8 French catheter and the second release member 620b may be configured to receive and/or releasably couple the second elongate medical device 690b, wherein the second elongate medical device 690b may be a 12 French catheter.

Figure 8A:
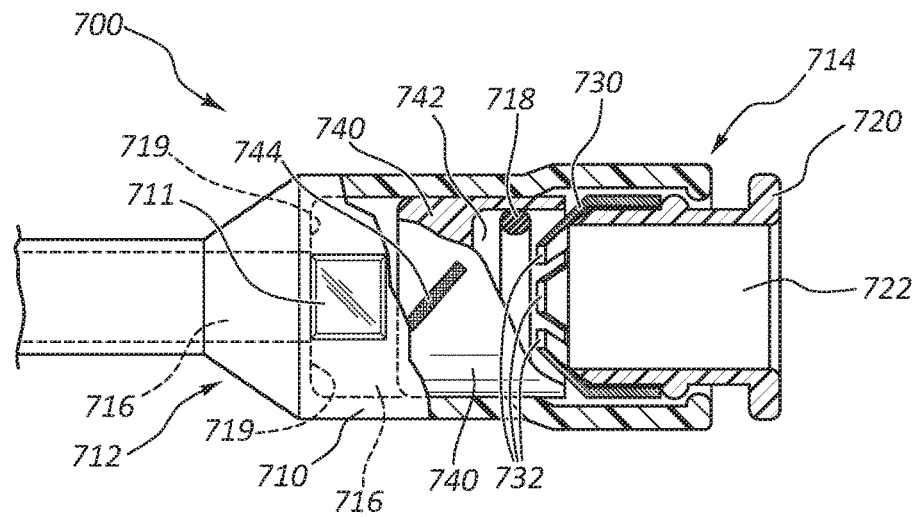
FIG. 8A is a partial cut-away view of a portion of a medical push connector in a first configuration.
Figure 8B:
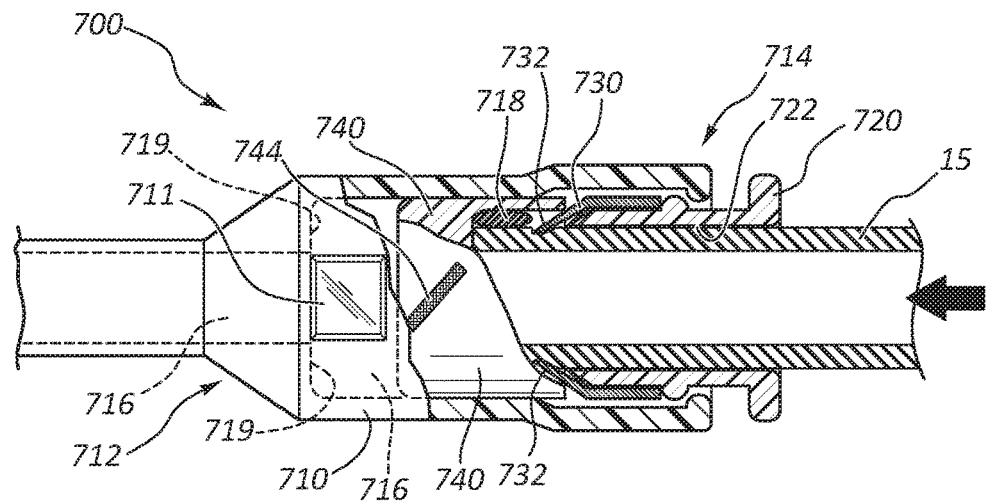
FIG. 8B is a partial cut-away view of the portion of the medical push connector of FIG. 8A in a second configuration.
Figure 8C:
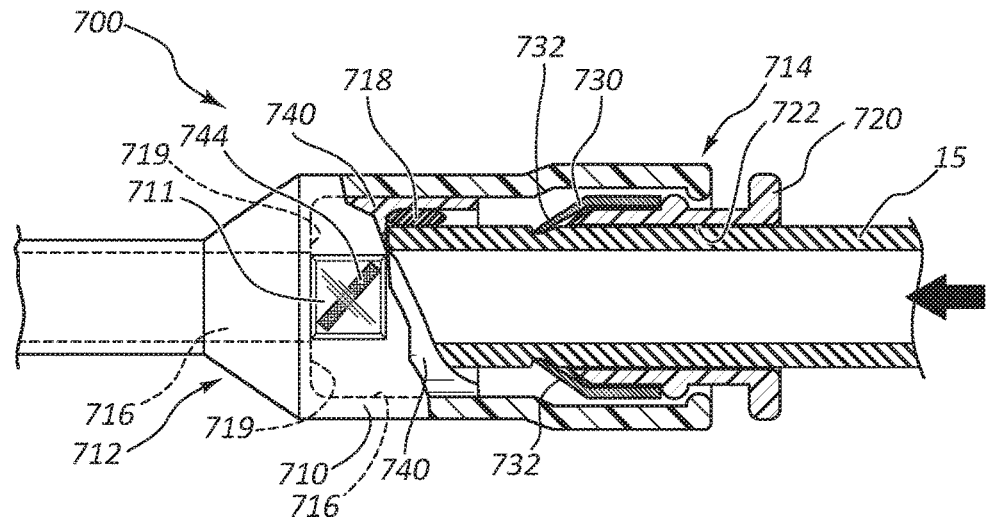
FIG. 8C is a partial cut-away view of the portion of the medical push connector of FIG. 8A in a third configuration.

FIG. 8A is a partial cut-away view of a portion of a medical connector 700, in a first configuration. FIG. 8B is the medical connector 700 in a second configuration and FIG. 8C depicts the medical connector 700 in a third configuration. As discussed above, the medical connector 700 can include a body 710 having a proximal end 712 and a distal end 714. Further, a body lumen 716 can extend through at least a portion of the body 710.

A release member 720 can be coupled to the body 710 at or adjacent the distal end 714 of the body 710. As shown, the release member 720 can include a release member lumen 722, wherein the release member lumen 722 is in communication with the body lumen 716. The medical connector 700 can further include an engagement member 730. In some embodiments, the engagement member 730 may be operatively coupled to the release member 720. In certain embodiments, the engagement member 730 may be configured to releasably couple a medical device to the medical connector 700. For example, with reference to FIGS. 8B and 8C, a practitioner may dispose at least a portion of an elongate medical device 15 within at least a portion of the release member lumen 722, and at least a portion of the engagement member 730 may be configured to engage at least a portion of the elongate medical device 15 such that the elongate medical device 15 is coupled to the medical connector 700.

As described above, the engagement member 730 can include one or more resilient elements 732. The one or more resilient elements 732 may be configured to engage a medical device when the medical device is disposed within at least a portion of the body lumen 716 (e.g., via the release member lumen 722). For example, the one or more resilient elements 732 may be configured to engage and/or interact with an outer surface of the elongate medical device 15.

In certain embodiments, the medical connector 700 may be configured to couple the elongate medical device 15 in a partial coupling state (see FIG. 8B). The medical connector 700 may also be configured to couple the elongate medical device 15 in a full or complete coupling state (see FIG. 8C). In the partial and/or full coupling states, the release member 720 may be disengaged from, or configured to be disengaged from, the one or more resilient elements 732 such that at least a portion of each of the one or more resilient elements 732 deflects radially inward relative to a longitudinal axis of the release member lumen 722.

The medical connector 700 may include a mechanism and/or components for indicating (e.g., to a practitioner) that the elongate medical device 15 (or another medical device) is fully disposed or "seated" within the medical connector 700. In some embodiments, the mechanism may be a visible mechanism. In some other embodiments, the mechanism may be audible, tactile, etc. As shown in FIGS. 8A-8C, the medical connector 700 can include an indicator member 740. The indicator member 740 can be disposed within at least a portion of the body lumen 716. Further, the indicator member 740 may be displaceable (e.g., slidably displaceable) within the body lumen 716. For example, upon engagement with the elongate medical device 15, the indicator member 740 may be displaced (e.g., proximally displaced) in relation to the body 710. In some embodiments, the indicator member 740 can include an indicator member lumen 742, wherein the indicator member lumen 742 is in communication (e.g., fluid communication) with the body lumen 716 and/or the release member lumen 722. Further, at least a portion of the indicator member lumen 742 may be configured to receive at least a portion of the elongate medical device 15.

In certain embodiments, a seal 718 (e.g., an O-ring seal) may be disposed within at least a portion of the indicator member 740. For example, the seal 718 may be disposed within at least a portion of the indicator member lumen 742. In various embodiments, the seal 718 may be configured to sealingly engage the elongate medical device 15 when at least a portion of the elongate medical device 15 is disposed within the indicator member lumen 742. For example, as shown in FIGS. 8B and 8C, the seal 718 may seal against an outside diameter of the elongate medical device 15.

An indicia 744 may be disposed (e.g., printed) on a portion of an outside surface of the indicator member 740. As illustrated, the indicia 744 is a printed diagonal bar or line. In some embodiments, the indicia 744 may be a circle, a square, a triangle, a number, a letter, or any other suitable shape or symbol. Furthermore, the indicator member 740 may be a first color (e.g., the indicator member 740 may be formed from a red material) and the indicia 744 may be a second color (e.g., the indicia 744 may be formed from a green material). In some embodiments, the indicator member 740 and the indicia 744 may be integral, and, in some other embodiments, the indicator member 740 and the indicia 744 may be discrete. Other combinations of colors and/or materials of the indicator member 740 and the indicia 744 are also within the scope of this disclosure. For example, the indicator member 740 may be printed with an orange ink and the indicia may be formed from a blue material.

With continued reference to FIGS. 8A-8C, the medical connector 700 can further include a window 711. The window 711 may be a transparent member disposed in at least a portion of a wall of the body 710. In some embodiments, an opening (instead of a window) may be disposed in a portion of the wall of the body 710. The window 711 can be aligned with the indicia 744, such that upon proximal displacement of the indicator member 740, the indicia 744 can be visible through the window 711. For example, a practitioner may be able to view the indicia 744 through the window 711 when the indicator member 740 has been displaced proximally in relation to the body 710.

The interaction between the window 711 and the indicia 744 can indicate to the practitioner if the elongate medical device 15 is only partially disposed within the medical connector 700 (see FIG. 8B) or if the elongate medical device 15 is fully disposed within the medical connector 700 (see FIG. 8C). In certain embodiments, if the elongate medical device 15 is only partially disposed within the medical connector 700, a full seal may not be formed between the elongate medical device 15 and the medical connector 700. Also, if the elongate medical device 15 is only partially disposed within the medical connector 700, the elongate medical device 15 may not be securely coupled to the medical connector 700. Accordingly, the indicator member 740, the indicia 744, and/or the window 711 may be configured to communicate and/or indicate to a practitioner if the medical connector 700 is in the full coupling state.

In some embodiments, at least a portion of the body 710 may be formed from a transparent material and at least a portion of the transparent material may be coated or printed to form a "window" in the body. That is, the window may be a portion of the body 710 that is not coated or printed. Accordingly, the indicia 744 may not visible through the body 710 (i.e., due to the printing) unless the indicia 744 is aligned with the unprinted window portion of the body 710.

With reference to FIG. 8B, the practitioner may dispose at least a portion of the elongate medical device 15 (as indicated by the arrow) through the release member lumen 722 of the release member 720 and into at least a portion of the indicator member lumen 742. As shown in FIG. 8B, the elongate medical device 15 is in the partial coupling state. Upon such a disposition of the elongate medical device 15, the indicator member 740 is displaced proximally in relation to the body 710; however, the indicia 744 is not visible through the window 711. In the partial coupling state, the indicia 744 may be partially visible through the window 711. Stated another way, a portion of the indicia 744 may be visible through the window 711 when the medical connector 700 and the elongate medical device 15 are in the partial coupling state.

With reference to FIG. 8C, the practitioner may fully (or substantially fully) dispose the elongate medical device 15 through the release member lumen 722 of the release member 720 and into the indicator member lumen 742. As shown in FIG. 8C, the elongate medical device is in the full coupling state. Upon such a disposition of the elongate medical device 15, the indicator member 740 is displaced proximally in relation to the body 710 such that the indicia 744 is fully (or substantially fully) visible through the window 711. In the full coupling state, the indicia 744 may be fully visible through the window 711 and indicate that the elongate medical device 15 is fully disposed or seated within the medical connector 700. Stated another way, substantially all of the indicia 744 may be visible through the window 711 when the medical connector 700 and the elongate medical device 15 are in the full coupling state.

The medical connector 700 may further include a proximal shoulder 719 disposed within a portion of the body lumen 716. The proximal shoulder 719 may interact with a proximal end of the indicator member 740 to provide a positive proximal stop for the indicator member 740 and/or the elongate medical device 15 with respect to the medical connector 700. For example, in the configuration shown in FIG. 8C the proximal end of the indicator member 740 is disposed in contact with the proximal shoulder 719.

As illustrated, the body lumen 716 of the medical connector 700 is substantially I-shaped. Stated another way, the body lumen 716 includes two openings, wherein one opening is disposed at or adjacent the distal end 714 of the body 710 and a second opening is disposed at or adjacent the proximal end 712 of the body 710. As stated above, other configurations of the medical connector 700 are also within the scope of this disclosure. For example, in some embodiments, the medical connector may include two or more release members and/or indicator members.

Other configurations of medical connectors, such as the medical connectors 100, 200, 300, 400, 500, 600, 700 are also within the scope of this disclosure. In certain embodiments, a medical connector may include a first release member on a first end of the medical connector and a second release member on a second end of the medical connector, and each of the first release member and the second release member may have substantially similar inside diameters and/or outside diameters. In some embodiments, a medical connector may only include a release member on one end of the medical connector (e.g., a first end) while the opposite end of the medical connector (e.g., a second end) includes another type of connector such as a luer connector, an interference fit connector, a snap connector, etc. In some other embodiments, a medical connector may include one release member on a first end of the medical connector and two release members on a second end of the medical connector. In yet some other embodiments, a medical connector may have four arms and a release member may be coupled to an end of each of the four arms.

Embodiments wherein the medical connector lacks release members are also within the scope of this disclosure. For example, a practitioner may desire that a patient be inhibited or prevented from uncoupling the medical connector from one or more medical devices. Stated another way, the medical connector may be "patient proof" such that a patient cannot transition the medical connector from the coupling state to the uncoupling state.

In some embodiments, the medical connector may include more than one body lumen. For example, the medical connector may include two, three, four, or more lumens. In certain embodiments, the medical connector may include one or more valves. For example, a valve may be disposed within at least a portion of the medical connector. The valve may be configured to inhibit or prevent flow of a fluid through the medical connector when the medical connector is uncoupled from another medical device. Upon coupling of the medical connector to the medical device the valve may be configured to transition from a closed state to an open state. Accordingly, the valve may only be configured to open when the medical connector is coupled to one or more other medical devices. Such a valve may limit or prevent a fluid from leaking through the medical connector when the medical connector is not coupled to a desired medical device (e.g., such as a drainage bag). Other configurations of medical connectors, release members, etc. are also within the scope of this disclosure.

The medical connectors of the present disclosure may enhance communication (e.g., fluid communication) between a first medical device and a second medical device, which are coupled via the medical connector, in relation to some other first and second medical devices, which may be coupled via other coupling mechanisms. For example, some other coupling mechanisms may include a barb, wherein a first end of the barb is disposed in an inner diameter of a portion of a first medical device and a second end of the barb is disposed in an inner diameter of a portion of a second medical device. Such a coupling mechanism can decrease the dimensions of at least a portion of the inner diameters of the first and second medical devices. Accordingly, fluid communication may be at least partially obstructed between the first medical device and the second medical device. In contrast, the medical connectors of the present disclosure can be disposed around an outer diameter of a portion of a first medical device and/or an outer diameter of a second medical device such that the dimensions of the inner diameters are not substantially altered or changed and fluid communication between each of the first medical device and the second medical device is not substantially obstructed and or inhibited.

Medical connectors according to the present disclosure may be formed in a variety of sizes. For example, as stated above, the medical connector may be sized so as to be coupled to an elongate medical device that is 4 French, 5 French, 6 French, 7 French, or any other suitable size. The medical connector may also include two or more release members and/or engagement members. Each of the release members and/or engagement members may be configured to couple a differently sized elongate medical device. That is, one end of the medical connector may be sized to couple an elongate medical device that is 6 French and another end of the medical connector may be sized to couple an elongate medical device that is 10 French. In contrast, some other coupling mechanisms (e.g., luer connectors) may only be available, for example, in two sizes or another limited number of sizes.

Methods of using the medical connectors are also disclosed herein. A catheter (e.g., a 10 French catheter) may be used for drainage. For example, the catheter may be used by a practitioner to drain a fluid from a cavity within a patient. The practitioner may cut the catheter and couple the cut end of the catheter to a first end of a medical connector. A second catheter (e.g., a catheter that is configured to empty into a drainage bag) may be coupled to a second end of the medical connector. Accordingly, the medical connector may be configured for use by the practitioner in a medical drainage procedure. In some embodiments, the drainage catheter may have a high flow level and the drainage catheter may be coupled via the medical connector to a drainage bag and/or a suction device (e.g., a vacuum).

In certain embodiments, drainage bags for use with medical connectors of the present disclosure may include a connection member for coupling the drainage bag to the medical connector. In various embodiments, the connection members may include a standard outside diameter such that the connection members may be coupled to the medical connectors. In various other embodiments, the connection members may include a variety of standardized outside diameters (e.g., there may be two, three, or more standard sizes of the outside diameters of the connection members).

In some embodiments, a practitioner may cut a catheter for length adjustment and the practitioner may use a medical connector to couple the cut end of the catheter to a second catheter or other medical device (e.g., a syringe). In contrast, in configurations wherein a catheter has a luer connector for coupling the catheter to a medical device the catheter may not be configured to be cut for length adjustment, as cutting the catheter may remove the luer connector. Medical connectors according to the present disclosure, however, may be coupled to a catheter that has been cut (e.g., for length adjustment).

In various embodiments, the medical connectors may be used with a high-pressure line or catheter (e.g., a line used in conjunction with a heart pump). The high pressure within the high-pressure line may exert a force on an internal surface of the high-pressure line (e.g., a radial force directed outwardly relative to a longitudinal axis of the high-pressure line). Such a force may at least slightly expand a wall of the high-pressure line such that a dimension of an outside diameter of the high-pressure line increases. Accordingly, the increased outside diameter of the high-pressure line may tend to "seat" an end of the line within a medical connector. Stated another way, an outside surface of the high-pressure line may be pressed against an inside surface of a portion of the medical connector and the coupling between each of the medical connector and the high-pressure line may be enhanced and/or strengthened. The medical connector according to the present disclosure may also be sufficiently strong and/or durable to couple a first line to a second line when a high pressure fluid is flowing between each of the first line and the second line.

As can be appreciated, additional methods and/or method steps can be derived from FIGS. 1-8C and the corresponding disclosure. Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially Y-shaped" is recited with respect to a feature, it is understood that in further embodiments, the feature can have a precisely Y-shaped configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, which changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical connector, comprising:
 a body having a first end and a second end, wherein the second end is configured to be coupled to a high-pressure fluid displacement medical device;
 a body lumen extending through the body between the first end and the second end wherein the body lumen is configured for communication with the high-pressure fluid displacement medical device;
 a first release member coupled to the first end of the body, the first release member comprising a first release member lumen in communication with the body lumen;
 a first engagement member operatively coupled to the first release member, the first engagement member deflectable in a radially outward direction to receive a first elongate medical device, the first engagement member configured to releasably couple the first elongate medical device to the medical connector;
 a second release member coupled to the second end of the body, the second release member comprising a second release member lumen in communication with the body lumen;
 a second engagement member operatively coupled to the second release member, the second engagement member deflectable in a radially outward direction to receive a second elongate medical device, the second engagement member configured to releasably couple the second elongate medical device to the medical connector; and
 a first seal disposed within the body lumen adjacent the first release member lumen, the first seal configured to sealingly engage the first elongate medical device when the first elongate medical device is disposed within the body lumen.

2. The medical connector of claim 1, further comprising:
 a second seal disposed within the body lumen adjacent the second release member lumen, the second seal configured to sealingly engage the second elongate medical device when the second elongate medical device is disposed within the body lumen.

3. The medical connector of claim 1, wherein the first release member lumen has a first inside diameter, wherein the second release member lumen has a second inside diameter, and wherein the first inside diameter is greater than the second inside diameter.

4. The medical connector of claim 1, wherein the medical connector is configured to sealably couple with the first elongate medical device and the second elongate medical device, and wherein an outside diameter of the first elongate medical device is greater than an outside diameter of the second elongate medical device.

5. The medical connector of claim 1, wherein the first engagement member comprises a resilient element, the resilient element configured to engage the first elongate medical device when the first elongate medical device is disposed within the first release member lumen, wherein the first release member is configured to engage the resilient element such that a portion of the resilient element deflects radially outward relative to a longitudinal axis of the first release member lumen in an uncoupling state, and wherein the first release member is further configured to be disengaged from the resilient element such that a portion of the resilient element deflects radially inward relative to a longitudinal axis of the first release member lumen in a coupling state.

6. The medical connector of claim 5, wherein the second engagement member comprises a resilient element, the resilient element configured to engage the second elongate medical device when the second elongate medical device is disposed within the second release member lumen,
 wherein the second release member is configured to engage the resilient element such that a portion of the resilient element deflects radially outward relative to a longitudinal axis of the second release member lumen in an uncoupling state, and wherein the second release member is further configured to be disengaged from the resilient element such that a portion of the resilient element deflects radially inward relative to a longitudinal axis of the second release member lumen in a coupling state.

7. A medical connector system, comprising: a medical connector, comprising:
 a body having a first end and a second end, wherein the second end is configured to be coupled to a high-pressure fluid displacement medical device;
 a body lumen extending through the body between the first end and the second end wherein the body lumen is configured for communication with the high pressure fluid displacement medical device;
 a first release member coupled to the first end of the body, the first release member comprising a first release member lumen in communication with the body lumen;
 a first engagement member operatively coupled to the first release member, the first engagement member deflectable in a radially outward direction;
 a second release member coupled to the second end of the body, the second release member comprising a second release member lumen in communication with the body lumen; and
 a second engagement member operatively coupled to the second release member, the second engagement member deflectable in a radially outward direction;
 a first seal disposed within the body lumen adjacent the first release member lumen, the first seal configured to sealingly engage the first elongate medical device when the first elongate medical device is disposed within the body lumen;
 a first elongate medical device configured to releasably couple with the first engagement member; and
 a second elongate medical device configured to releasably couple with the second engagement member.

8. The medical connector system of claim 7, wherein the first release member lumen has a first inside diameter, wherein the second release member lumen has a second inside diameter, and wherein the first inside diameter is greater than the second inside diameter.

9. The medical connector of claim 7, wherein the medical connector is configured to sealably couple with the first elongate medical device and the second elongate medical device, and wherein an outside diameter of the first elongate medical device is greater than an outside diameter of the second elongate medical device.

10. A medical connector, comprising:
a body having a first end and a second end, wherein the second end is configured to be coupled to a high-pressure fluid displacement medical device;
a body lumen extending through the body between the first end and the second end wherein the body lumen is configured for communication with the high-pressure fluid displacement medical device;
a first release member coupled to the first end of the body, the first release member comprising a first release member lumen in communication with the body lumen;
a first engagement member operatively coupled to the first release member, the first engagement member deflectable in a radially outward direction to receive a first elongate medical device, the first engagement member configured to releasably couple the first elongate medical device to the medical connector;
a second release member coupled to the second end of the body, the second release member comprising a second release member lumen in communication with the body lumen; and
a second engagement member operatively coupled to the second release member, the second engagement member deflectable in a radially outward direction to receive a second elongate medical device, the second engagement member configured to releasably couple the second elongate medical device to the medical connector;
wherein the first engagement member comprises a resilient element, the resilient element configured to engage the first elongate medical device when the first elongate medical device is disposed within the first release member lumen, wherein the first release member is configured to engage the resilient element such that a portion of the resilient element deflects radially outward relative to a longitudinal axis of the first release member lumen in an uncoupling state, and wherein the first release member is further configured to be disengaged from the resilient element such that a portion of the resilient element deflects radially inward relative to a longitudinal axis of the first release member lumen in a coupling state.

11. The medical connector of claim 10, further comprising:
a first seal disposed within the body lumen adjacent the first release member lumen, the first seal configured to sealingly engage the first elongate medical device when the first elongate medical device is disposed within the body lumen.

12. The medical connector of claim 11, further comprising:
a second seal disposed within the body lumen adjacent the second release member lumen, the second seal configured to sealingly engage the second elongate medical device when the second elongate medical device is disposed within the body lumen.

13. The medical connector of claim 10, wherein the first release member lumen has a first inside diameter, wherein the second release member lumen has a second inside diameter, and wherein the first inside diameter is greater than the second inside diameter.

14. The medical connector of claim 10, wherein the medical connector is configured to sealably couple with the first elongate medical device and the second elongate medical device, and wherein an outside diameter of the first elongate medical device is greater than an outside diameter of the second elongate medical device.

15. The medical connector of claim 10, wherein the second engagement member comprises a resilient element, the resilient element configured to engage the second elongate medical device when the second elongate medical device is disposed within the second release member lumen, wherein the second release member is configured to engage the resilient element such that a portion of the resilient element deflects radially outward relative to a longitudinal axis of the second release member lumen in an uncoupling state, and wherein the second release member is further configured to be disengaged from the resilient element such that a portion of the resilient element deflects radially inward relative to a longitudinal axis of the second release member lumen in a coupling state.

* * * * *